(12) United States Patent
Freyman et al.

(10) Patent No.: US 8,518,682 B2
(45) Date of Patent: *Aug. 27, 2013

(54) MICROENCAPSULATED COMPOSITIONS FOR ENDOLUMINAL TISSUE ENGINEERING

(75) Inventors: Toby M. Freyman, Waltham, MA (US); Joseph A. Levendusky, Groton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 126 days.

This patent is subject to a terminal disclaimer.

(21) Appl. No.: 12/966,711

(22) Filed: Dec. 13, 2010

(65) Prior Publication Data

US 2011/0189240 A1 Aug. 4, 2011

Related U.S. Application Data

(63) Continuation of application No. 11/073,433, filed on Mar. 7, 2005, now Pat. No. 7,851,189.

(51) Int. Cl.
  *C12N 11/04* (2006.01)
(52) U.S. Cl.
  USPC ........... 435/177; 435/180; 435/182; 424/425; 424/93.7
(58) Field of Classification Search
  None
  See application file for complete search history.

(56) References Cited

U.S. PATENT DOCUMENTS

| | | | |
|---|---|---|---|
| 4,938,763 A | 7/1990 | Dunn et al. | |
| 5,075,109 A | 12/1991 | Tice et al. | |
| 5,084,350 A | 1/1992 | Chang et al. | |
| 5,460,939 A | 10/1995 | Hansbrough et al. | |
| 5,599,788 A | 2/1997 | Purchio et al. | |
| 5,620,883 A | 4/1997 | Shao et al. | |
| 5,695,998 A | 12/1997 | Badylak et al. | |
| 5,733,925 A | 3/1998 | Kunz et al. | |
| 5,879,709 A | 3/1999 | Soon-Shiong et al. | |
| 6,156,572 A | 12/2000 | Bellamkonda et al. | |
| 6,544,227 B2 | 4/2003 | Sahatjian et al. | |
| 6,565,530 B2 | 5/2003 | Sahatjian et al. | |

(Continued)

FOREIGN PATENT DOCUMENTS

| | | |
|---|---|---|
| CA | 1215922 | 12/1986 |
| EP | 0 418 796 A1 | 3/1991 |

(Continued)

OTHER PUBLICATIONS

Sefton et al., "Making microencapsulation work: conformal coating, immobilization gels and in vivo performance" Journal of Controlled Release (2000) vol. 65, pp. 173-186.

(Continued)

*Primary Examiner* — Allison Ford
(74) *Attorney, Agent, or Firm* — Mayer & Williams PC; David B. Bonham

(57) ABSTRACT

A tissue engineering composition adapted for application to an interior surface of a body lumen of a patient. The composition comprises (a) a carrier medium that is adapted to flow and to stably adhere the composition to the body lumen and (b) microcapsules, which are dispersed within the carrier medium and which contain one or more living cells encapsulated within a coating that includes a biodegradable polymer. The composition promotes growth of the cells on the lumen surface subsequent to application of the composition to the lumen.

23 Claims, 2 Drawing Sheets

(56) References Cited

U.S. PATENT DOCUMENTS

| | | |
|---|---|---|
| 6,905,875 B2 * | 6/2005 | Yu et al. .................. 435/395 |
| 2001/0047147 A1 | 11/2001 | Slepian et al. |
| 2002/0022016 A1 | 2/2002 | Walsh et al. |
| 2002/0094569 A1 | 7/2002 | Yu et al. |
| 2002/0099332 A1 | 7/2002 | Slepian et al. |
| 2003/0087111 A1 | 5/2003 | Hubbell et al. |
| 2004/0009212 A1 | 1/2004 | Tsai |
| 2004/0083006 A1 | 4/2004 | Ellingsen et al. |
| 2004/0086493 A1 | 5/2004 | Hubbell et al. |
| 2004/0106987 A1 | 6/2004 | Palasis et al. |
| 2004/0126405 A1 | 7/2004 | Sahatjian et al. |
| 2004/0132143 A1 | 7/2004 | DeAngelis et al. |
| 2005/0002915 A1 | 1/2005 | Atala et al. |
| 2005/0042254 A1 | 2/2005 | Freyman et al. |
| 2006/0251630 A1 | 11/2006 | Stewart et al. |
| 2006/0286141 A1 | 12/2006 | Campbell |

FOREIGN PATENT DOCUMENTS

| | | |
|---|---|---|
| WO | WO 91/01720 | 2/1991 |
| WO | 9300076 A1 | 1/1993 |
| WO | 9523591 A1 | 9/1995 |
| WO | 9627367 A1 | 9/1996 |
| WO | 0066089 A1 | 11/2000 |
| WO | 02060315 A2 | 8/2002 |
| WO | 2004032881 A2 | 4/2004 |
| WO | 2004058305 A2 | 7/2004 |
| WO | 2004110347 A2 | 12/2004 |

OTHER PUBLICATIONS

Abstract. H.W. Matthew et al., "Complex Coacervate Microcapsules for Mammalian Cell Culture and Artificial Organ Development," Biotechnol. Prog., vol. 9, No. 5, Sep.-Oct. 1993, pp. 510-519.

Abstract. Sun-Hee Yu et al., "Encapsulation of Rat Hepatocyte Speroids for the Development of Artificial Liver," Biotechnology Techniques, vol. 13, No. 9, Sep. 1999, pp. 609-614.

T.M.S. Chang et al., "Microencapsulation of Enzymes, Cells and Genetically Engineered Microorganisms Methods," Molecular Biotechnology, vol. 17, 2001, pp. 1-13.

Hasan Uludag et al., "Technology of Mammalian Cell Encapsulation," Advanced Drug Delivery Reviews, vol. 42, 2000, pp. 29-64.

Abstract. L. Canaple et al., "Maintenance of Primary Murine Hepatocyte Functions in Multicomponent Polymer Capsules—in Vitro Cryopreservation Studies," J. Hepatol., vol. 34, No. 1, Jan. 2001, pp. 148-149.

Abstract. L.H. Mei et al., "Cultivation and Modeling of Encapsulated *Saccharomyces cerevisiae* in NaCS-PDMDAAC Polyelectrolyte Complexes," vol. 19, No. 4, Jul.-Aug. 2002, pp. 397-405.

R.V. Muralidhar et al., "Development of High Density Cultivation Systems by Bioencapsulation," Current Science, vol. 81, No. 3, Aug. 10, 2001, pp. 263-269.

Alberto Diaspro et al., "Microscopical Characterization of Nanocapsules Templated on Ionic Crystals and Biological Cells Toward Biomedical Applications," IEEE Transactions on Nanobioscience, vol. 1, No. 3, Sep. 2002, pp. 110-115.

Abstract. J. Stange et al., "Prolonged Biochemical and Morphological Stability of Encapsulated Liver-Cells-A New Method," vol. 21, No. 3, 1993, pp. 343-352.

* cited by examiner

MICROENCAPSULATED COMPOSITIONS FOR ENDOLUMINAL TISSUE ENGINEERING

STATEMENT OF RELATED APPLICATIONS

This application is a continuation of U.S. patent application Ser. No. 11/073,433, filed Mar. 7, 2005, which is incorporated by reference herein in its entirety.

FIELD OF THE INVENTION

The present invention is directed to tissue engineering compositions, and more particularly tissue engineering compositions for endoluminal application.

BACKGROUND OF THE INVENTION

Over the-past decade, tissue engineering has evolved from a loose collection of different disciplines to a biotechnology field in its own right. A combination of chemical engineering and cell biology, with input from genetics, surgery and other disciplines, tissue engineering combines living cells, biological and synthetic materials into implants that can function in the human body. Researchers have taken the first steps toward creating semisynthetic, living organs such as livers, hearts, and pancreases by culturing colonies of living hepatocytes, cardiomyocytes, and islet cells, respectively.

An endoluminal procedure is a medical procedure which takes place in one of the many hollow spaces, or lumens, within the human body. These procedures may take place, for example, in vascular, gastrointestinal (GI), or air exchange lumens, among others, and they may involve disease diagnosis and/or treatment. Millions of endoluminal procedures are performed each year in hospitals around the world. Endoluminal procedures are often performed utilizing devices such as endoscopes and catheters.

Researchers introduced microencapsulation of engineered tissue in the late 1970's. Microcapsules are easy to produce and have been used in the delivery of everything from agricultural chemicals, cosmetics and fragrances to pharmaceuticals and medicines. The use of microencapsulated engineered tissue has been generally confined to providing immuno-isolation for tissue implants that either produce a therapeutic substance (e.g., the use of pancreatic islet cells for producing insulin), or which perform a metabolic function (e.g., the use of hepatocytes for plasma detoxification). Fabricators of microcapsules commonly aim for a membrane pore size that will allow diffusion of molecules of molecular weight up to 50,000 daltons. Such pore sizes generally are small enough to block invasion by immune cells and most immune molecules, but are large enough to allow the inflow of nutrients and oxygen and the outflow of cellular byproducts. Encapsulation of this form is generally meant to be permanent, lasting for the lifetime of the encapsulated tissue and/or the length of therapy required.

SUMMARY OF THE INVENTION

The present invention combines various aspects of tissue engineering, microencapsulation and endoluminal techniques.

According to an aspect of the invention, a tissue engineering composition is provided, which is adapted for application to an interior surface of a body lumen of a patient. The composition comprises (a) a carrier medium that is adapted to flow and to stably adhere the composition to the body lumen and (b) microcapsules, which are dispersed within the carrier medium and which contain one or more living cells encapsulated within a coating that includes a biodegradable polymer. The composition promotes growth of the cells on the lumen surface subsequent to application of the composition to the lumen.

These and other embodiments and advantages of the present invention will become immediately apparent to those of ordinary skill in the art upon review of the Detailed Description and Claims to follow.

DETAILED DESCRIPTION

A more complete understanding of the present invention is available by reference to the following detailed description of the embodiments. The detailed description of the embodiments which follows is intended to illustrate but not limit the invention. The scope of the invention is defined by the appended claims.

The present invention is directed to tissue engineering compositions, and more particularly to tissue engineering compositions for application to surfaces of various body lumens. The compositions of the present invention contain a carrier medium with microcapsules dispersed within the carrier medium. The microcapsules include a core containing one or more living cells, which is encapsulated within a biodegradable coating. The compositions of the present invention are adapted to attach to interior surfaces of body lumens, where they subsequently promote cell growth at or near the lumen surface.

Figure 1:
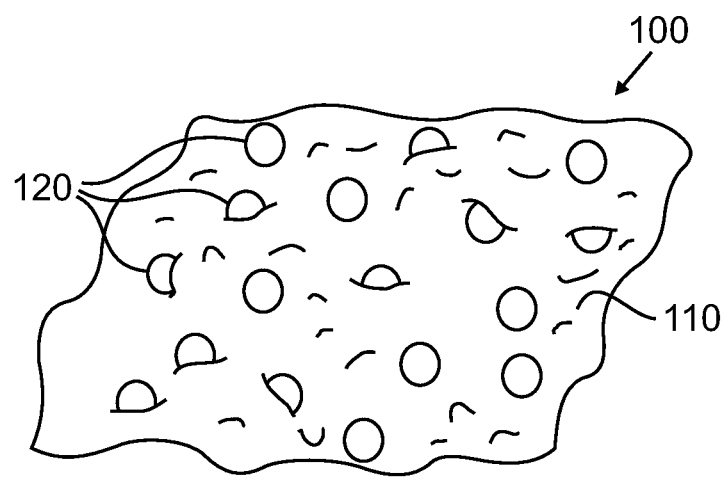
FIG. 1 is a schematic illustration of a tissue engineering composition in accordance with an embodiment of the present invention.

A specific example of one such tissue engineering composition 100 is schematically illustrated in FIG. 1, in which the carrier medium 110 and a plurality of microcapsules 120 are shown.

The compositions of the present invention are adapted for delivery to a wide range of endoluminal surfaces, including the following: lumens of the cardiovascular system such as the heart, arteries (e.g., coronary, femoral, aorta, ilial, carotid and vertebro-basilar arteries) and veins, lumens of the genitourinary system such as the urethra (including prostatic urethra), bladder, ureters, vagina, uterus, spermatic and fallopian tubes, the nasolacrimal duct, the eustachian tube, lumens of the respiratory tract, such as the trachea, bronchi, nasal passages and sinuses, lumens of the gastrointestinal tract such as the esophagus, gut, duodenum, small intestine, large intestine, colon, biliary and pancreatic duct systems, lumens of the lymphatic system, the major body cavities (peritoneal, pleural, pericardial) and so forth.

The cells that are encapsulated in the compositions of the present invention include mature and immature endothelial cells, muscle cells, connective tissue cells, and nerve cells. The specific cells selected for use in the compositions will depend upon the luminal tissue that is being treated.

Examples of cells include both differentiable and undifferentiated (mature and immature) cells, such as the following: (a) differentiable cells and sources of the same including totipotent, pluripotent, multipotent, and progenitor stem cells, side population cells, lineage negative cells such as $CD34^-$ cells, $CD34^+$ cells and $cKit^+$ cells, mesenchymal stem cells, mesenchymal stem cells with 5-aza, cord blood cells, cardiac and other tissue derived stem cells, whole bone marrow, bone marrow mononuclear cells, endothelial progenitor cells, multipotent adult progenitor cells, skeletal myoblasts (also known as satellite cells), muscle derived cells, go cells, adult cardiac fibroblasts plus 5-aza, MyoD scar fibroblasts, genetically modified differentiable cells such as pacing cells, embryonic stem cells, embryonic stem cells clones, fetal/neonatal cells, and teratoma derived cells, (b) squamous epithelial cells, such as non-keratinized squamous endothelial cells, for example, those lining the upper GI tract (e.g., cheek and esophagus) and lung alveoli, as well as the mesothelium lining of various major body cavities (e.g., peritoneal, pleural, pericardial) and the endothelium lining the heart, blood vessels, sinusoids and lymphatics, (c) cuboidal epithelial cells, which frequently line glandular ducts, (d) columnar epithelial cells, such as those lining portions of the digestive tract (e.g., the stomach and small intestines), the female reproductive tract (e.g., the uterus and fallopian tubes), as well as numerous other surfaces, (e) pseudostratified columnar epithelial cells, such as those lining portions of the respiratory tract (e.g., trachea) and ducts of the male reproductive system, (f) transitional epithelial cells, such as those lining the distensible walls of the urinary tract (e.g., the renal pelvis, ureters, bladder and urethra), (g) glandular epithelium, (h) smooth muscle cells, which lie beneath epithelial cells in many body lumens such as many of those found in the vasculature, the genitourinary system, respiratory tract, and gastrointestinal tract, (i) cardiomyocytes, and (j) connective tissue cells such as fibroblasts.

Microcapsules suitable for use in the present invention have a wide range of sizes, for example, ranging from the dimension of a single cell (e.g., 5 to 20 microns) up to 1000 microns.

In general, microcapsules for use in conjunction with the compositions of the present invention are permeable to nutrients, oxygen and other materials necessary to support the normal metabolic functions of the cells. The membrane also is generally permeable to cellular products, including various metabolic byproducts. In this way, cells remain viable if placed within a suitable environment, such as culture medium or a host organism. The membrane permeability is also preferably sufficient to preclude entry of lymphocytes, large proteins, and other entities associated with the immunological reactions that typically result in rejection of the cells from the host's immune system. Moreover, encapsulation protects the enclosed cells from mechanical damage due to pressure drops and shear stresses that can occur during delivery to the body (e.g., from a medical device such as a catheter), and the resulting microcapsules form a matrix that gives the compositions of the present invention substance, aiding in the formation of an adhesive and cohesive region at the treatment site.

Encapsulation of mammalian cells has been practiced for several decades. Numerous encapsulation techniques have been developed over the years. Well known techniques involve direct layer-by-layer encapsulation techniques, interfacial capsule formation techniques (e.g., complex coacervation, interfacial precipitation, interfacial polymerization), and core formation (e.g., by thermoreversible gelation, crosslinking, polymerization, etc.) with subsequent encapsulation, among other techniques.

Many techniques for encapsulation of living cells involve the interaction of oppositely charged species. Because they are soluble in water, charged species (e.g., cations, anions, zwitterions, and polyelectrolytes), offer the feasibility of developing an aqueous encapsulation system that is relatively biocompatible with the cells to be encapsulated, thereby avoiding death or serious injury to the cells during processing.

Polyelectrolytes are polymers that have a number of charged (e.g., ionically dissociated) groups. Usually, the number of these groups in the polyelectrolytes is so large that the polymers in dissociated form (also called polyions) are water-soluble. Depending on the type of dissociable groups, polyelectrolytes are typically classified as polyacids and polybases.

When dissociated, typically at the physiological pH of the cells to be encapsulated, polyacids form polyanions, with protons being split off. Polyacids include inorganic, organic and biological polymers. Examples of polyacids include polyphosphoric acids, polyvinylsulfuric acids, polyvinylsulfonic acids, polyvinylphosphonic acids and polycarboxylic acids. Examples of the corresponding salts, which are also called polysalts or polyanions, are polyphosphates, polyvinylsulfates, polyvinylsulfonates, polyvinylphosphonates and polycarboxates. Polybases, on the other hand, contain groups which are capable of accepting protons, e.g., by reaction with acids, with a salt being formed, typically at the physiological pH of the cells to be encapsulated. Examples of polybases having dissociable groups include polyallylamine, polyethylimine, polyvinylamine and polyvinylpyridine. By accepting protons, polybases form polycations.

Suitable polyelectrolytes for use in the invention include those based on biological polymers and those based on synthetic polymers. Linear or branched polyelectrolytes can be used. Using branched polyelectrolytes can lead to less compact polyelectrolyte multilayers having a higher degree of wall porosity. Suitable polyelectrolytes include relatively low-molecular weight polyelectrolytes (e.g., polyelectrolytes having molecular weights of a few hundred Daltons) up to macromolecular polyelectrolytes (e.g., polyelectrolytes of biological origin, which commonly have molecular weights of several million Daltons).

Specific examples of positively charged polyelectrolytes include poly-l-lysine and other polyamino acids having a net positive charge at physiological pH such as positively charged gelatin, spermidine, poly(ornithine), poly(arginine), poly(histidine), other polypeptides and proteins, and positively charged polysaccharides such as chitosan, among others. Specific examples of negatively charged polyelectrolytes include alginates such as sodium alginate, polyglycolic acid (PGA), polylactic acid (PLA), poly-2-hydroxy-butyrate (PHB), polycaprolactone (PCL), poly(lactic-co-glycolic) acid (PLGA), protamine sulfate, albumin, carrageenan, furcellaran, pectin, xanthan, hyaluronic acid, sodium carboxymethyl cellulose, heparin, heparan sulfate, negatively charged gelatin, various cellulose derivatives such as those discussed below, for example, sodium carboxymethylcellulose, chondroitin sulfate, dermatan sulfate, dextran sulfate, DNA, and RNA, among others.

By using bioabsorbable polyelectrolytes for encapsulation, cellular release can be controlled in various embodiments based on the rate of degradation of the polyelectrolyte layer(s). As used herein, a "bioabsorbable" material is a material which undergoes degradation, resorption and/or other disintegration processes upon administration to a patient over a period of time. Depending on the condition to be treated, this period is generally less than one year ranging, for example, from 1 day to 2 days to 4 days to 1 week to 2 weeks to 1 month to 2 months to 4 months to 6 months to 8 months to 1 year, as well as all points in between (the "degradation period").

In certain embodiments of the invention, individual cells or cell aggregates are conformally coated using various known layer-by-layer techniques. Layer-by-layer techniques involve coating substrates (here, cells or aggregates of cells) using polyelectrolyte materials via electrostatic self-assembly. In the layer-by-layer technique, a first polyelectrolyte layer having a first net charge is typically deposited on an underlying substrate, followed by a second polyelectrolyte layer having a second net charge that is opposite in sign to the net charge of the first polyelectrolyte layer, and so forth. The charge on the outer layer is reversed upon deposition of each sequential polyelectrolyte layer.

For instance, cell surfaces frequently carry a net negative charge. Thus, by incubating cells in a solution containing a positively charged polyelectrolyte, it is possible to deposit a layer of the charged polyelectrolyte on the negatively charged cell surfaces. In general, the solution will contain a suitable aqueous solvent that does not adversely affect viable cells. Such solvents are well known and include buffered saline, culture medium and the like. After exposure to the solution, the cell surfaces are washed to remove excess polycation and subsequently exposed to a solution of negatively charged polyelectrolyte to form a polyanion layer. In this way, multiple layers can be provided. Successive exposure to solutions of oppositely charged polyelectrolytes will create as many layers as is desired.

As a specific example, S. cerevisiae have been encapsulated using poly(styrene sulfonate) as a polyanion and poly (allylamine hydrochloride) as a polycation. See A. Diaspro et al., IEEE Trans. on Nanobioscience, Vol. 1, No. 3, September 2002, pp. 110-1115. S. cerevisiae have also been encapsulated using sodium cellulose sulfate as a polyanion and poly (dimethyldiallylammonium chloride) as a polyanion. The results showed that the encapsulated microorganisms had the same growth trends as in free cell culture. See Mei L H and Yao S J. "Cultivation and modelling of encapsulated *Saccharomyces cerevisiae* in NaCS-PDMDAAC polyelectrolyte complexes," J. Microencapsul. 2002 July-August; 19(4):397-405.

Figure 2:
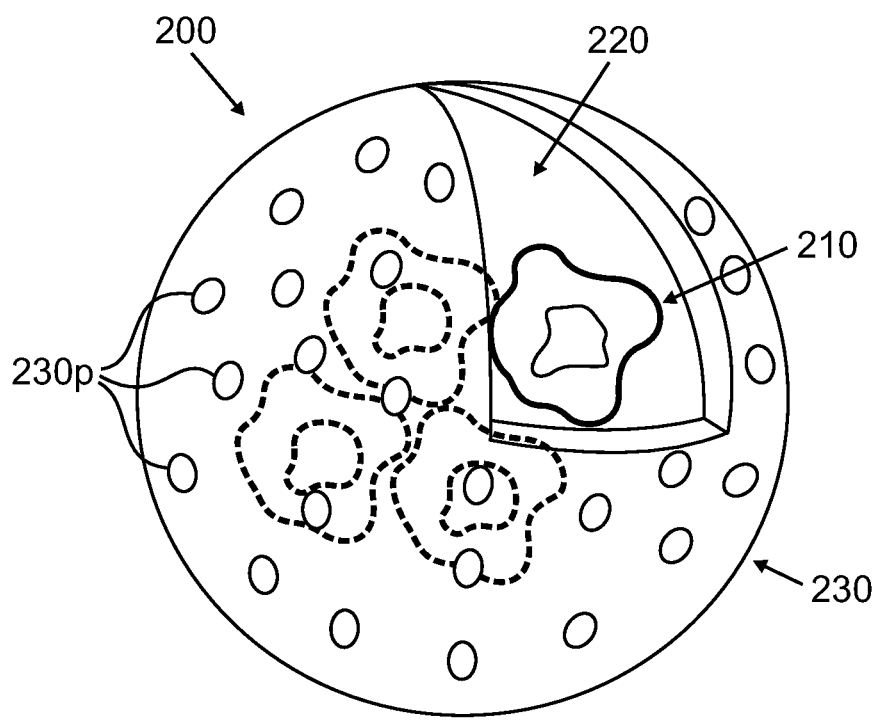
FIG. 2 is a schematic illustration of a microcapsule for use in the tissue engineering compositions of the present invention.

In other embodiments, a plurality of cells or cell aggregates are provided within an inner core material, which is encapsulated within a porous shell. A specific example of a microcapsule 200 of this type is schematically illustrated in FIG. 2. Within the microcapsule 200, is an inner core material 220 (e.g., an aqueous liquid core, a crosslinked or polymerized core, or a core material of another type such as a gel core). A plurality of cells 210 (e.g., epithelial cells such as squamous epithelial cells) are present in the inner core material 220. The inner core material 220 is encapsulated by a porous shell 230 (e.g., a porous polyelectrolyte shell), in which the pores 230p are schematically illustrated.

Various encapsulation techniques have been developed for forming such microcapsules, including interfacial capsule formation techniques (e.g., complex coacervation, interfacial precipitation, interfacial polymerization), and core formation (e.g., by thermoreversible gelation, crosslinking, polymerization, etc.) with subsequent encapsulation, among other techniques.

For instance, complex coacervation is a technique that involves the electrostatic interaction of two oppositely charged polyelectrolytes. In this technique, the electrostatic interaction between the two species of macromolecules results in the separation of a polymer-rich phase, or "coacervate," from a polymer-poor phase, or "supernatant." The encapsulation process can be performed in aqueous solution at ambient temperatures, and no crosslinking reaction is necessary.

As a specific example, cells can be provided within a first solution that is formed by dissolving a first polyelectrolyte of first charge in a suitable aqueous solvent. Upon exposing droplets of this first solution to a second solution, which contains a second polyelectrolyte of opposite charge to that of the first polyelectrolyte, a capsule is formed at the interface between the first and second solutions. Once microcapsules are formed in this fashion, additional layers can be added using, for example, the layer-by-layer assembly techniques as discussed above. Proper matching of polyelectrolytes can readily be confirmed, for example, by adding a drop of a solution of first polyelectrolyte to a solution of the second polyelectrolyte. If the polyelectrolytes are properly matched, a microcapsule will rapidly form at the interface between the first and second solutions. Whether or not a given encapsulation structure provides sufficient permeability can readily be determining by in vitro tests using standard cell culture media. For more information see, e.g., U.S. Patent Application No. 2002/0094569 to Yu et al. Further layers can be provided using layer-by-layer self assembly as discussed above.

Encapsulation via coacervation techniques has been conducted using a variety of polyanion-polycation combinations. One encapsulation structure formed using (carboxymethyl) cellulose, chondroitin sulfate A, chitosan, and polygalacturonate was found to be superior to alginate-polylysine microcapsules (discussed below) and supported the long-term survival and growth of liver endothelial cells. See H. W. Matthew et al., "Complex coacervate microcapsules for mammalian cell culture and artificial organ development," Biotechnol Prog. 1993 September-October; 9(5):510-9.

In another study, male Wistar rat hepatocytes were encapsulated using cellulose sulphate and polydimethyldialyllammonium chloride as polyelectrolytes. Amino acid metabolism rate and urea synthesis of the cells increased over the investigation period, in contrast to decrease observed in control monolayer cultures. Stange et al., "Prolonged biochemical and morphological stability of encapsulated liver cells—a new method." Biomater Artif Cells Immobilization Biotechnol. 1993; 21(3):343-52.

In another study, polyelectrolyte complexation of sodium alginate, cellulose sulphate and poly(methylene-co-guanidine) hydrochloride was used to encapsulate murine hepatocytes. These capsules were not cytotoxic and showed good biocompatibility towards primary murine hepatocytes. Canaple L, et al., "Maintenance of primary murine hepatocyte functions in multicomponent polymer capsules: in vitro cryopreservation studies." J Hepatol 2001; 34:11-8.

Finally, hepatocyte spheroids and hepatocytes have been immobilized in chitosan/alginate capsules formed by the electrostatic interactions between chitosan and alginate. See Yu et al., "Encapsulation of rat hepatocyte spheroids for the development of artificial liver" Biotechnology Techniques 13 (9): 609-614, September 1999.

Techniques are also known, other than coacervation, in which capsules are formed around cores containing multiple cells or cell aggregates. For example, interfacial precipitation has been used to form microencapsulates of mammalian cells. In this method, a cell suspension and a polymer solution are extruded separately, for example, through two concentrically configured needles, thereby forming a core of the cell suspension with a surrounding liquid shell of polymer solution. The core-and-shell droplets are dropped into a bath whereby the polymer solvent is extracted thereby resulting in the precipitation of a solid shell. Organic solvents such as dimethyl sulfoxide (DMSO), dimethyl formamide (DMF), dimethyl acetamide (DMAc), diethyl phthalate, and acetone are used to dissolve the organic polymers. Contact of cells with organic solvents is unavoidable, but contact can be minimized using various coextrusion schemes. For further details, see e.g., Hasan Uludag et al., "Technology of mammalian cell encapsulation," *Advanced Drug Delivery Reviews* 42 (2000) 29-64. Once a solid shell is formed, additional layers can be provided, for example, by polyelectrolyte layer self assembly techniques.

It is also known to expose droplets of a cell-containing polyelectrolyte solution to a solution that contains a crosslinking agent, which crosslinks the polyelectrolyte solution thereby forming solid beads. As above, once a solid bead is formed, it can be encapsulated by one or more layers, for example, by polyelectrolyte layer self assembly techniques. Crosslinking agents include ionic and covalent crosslinking agents.

For example, in some embodiments, polyelectrolytes are ionically crosslinked, for instance, with polyvalent ions. Suitable crosslinking ions include polyvalent cations selected from the group consisting of calcium, magnesium, barium, strontium, boron, beryllium, aluminum, iron, copper, cobalt, lead and silver cations ions. Polyvalent anions include phosphate, citrate, borate, succinate, maleate, adipate and oxalate anions.

In other embodiments, polymers are covalently crosslinked, for example, using a polyfunctional crosslinking agent that is reactive with functional groups in the polymer structure. The polyfunctional crosslinking agent can be any compound having at least two functional groups that react with functional groups in the polymer. A common crosslinking agent is glutaraldehyde. Covalent crosslinking agents are by nature, more chemically aggressive than ionic crosslinking agents.

Suitable polymers for ionic and/or covalent crosslinking (many of which are polyelectrolytes that are also suitable for coacervation) can be selected, for example, from the following: polyacrylates; poly(acrylic acid); poly(methacrylic acid); polyacrylamides; poly(N-alkylacrylamides); polyalkylene oxides; poly(ethylene oxide); poly(propylene oxide); poly(vinyl alcohol); poly(vinyl aromatics); poly(vinylpyrrolidone); poly(ethylene imine); poly(ethylene amine); polyacrylonitrile; poly(vinyl sulfonic acid); polyamides; poly(L-lysine); hydrophilic polyurethanes; maleic anhydride polymers; proteins; collagen; elastin; cellulose and its derivatives including methyl cellulose, ethyl cellulose, carboxymethyl cellulose, hydroxymethyl cellulose, cellulose acetate, and cellulose sulfate sodium salt; dextran; carboxymethyl dextran; modified dextran; alginates; alginic acid; pectinic acid; hyaluronic acid; hyalobiuronic acid; heparin; chitin; chitosan; pullulan; agarose; agar; gelatin; gellan; xanthan; curdlan; carboxymethyl starch; hydroxyethyl starch; chondroitin sulfate; guar; starch; carageenan and salts, copolymers, mixtures and derivatives thereof.

In accordance with one well known technique, droplets containing cells or cell aggregates and sodium alginate are dropped into a solution of divalent cations (e.g., calcium or barium ions), which results in gelation of the alginate into beads. Because the alginate is negatively charged, a layer of polycationic material, such as poly-l-lysine can be applied by simply washing the beads and introducing them into a polycation solution. See e.g., Hasan Uludag et al., "Technology of mammalian cell encapsulation," *Advanced Drug Delivery Reviews* 42 (2000) 29-64.

In still other embodiments, cells or cell aggregates are dispersed in a material which is a liquid at a first temperature, but which produces beads when cooled. One well known example of such a material is agarose. As above, once a bead is formed, one or more encapsulation layers are provided.

Conversely, in still other embodiments, cells or cell aggregates are dispersed in a material that exists as a liquid at temperatures a first temperature, but which are converted to a gel when heated. The temperature at which a transition from liquid to gel occurs is sometimes referred to as the lower critical solution temperature (LCST), and it can be a small temperature range as opposed to a specific temperature. Materials possessing an LCST are sometimes referred to as LCST materials. Typical LCST's for the practice of the present invention range, for example, from 10 to 40° C. Suitable LCST materials include, for example, poly(oxyalkene) polymers and copolymers such as poly(ethylene oxide)poly(propylene oxide) (PEO-PPO) copolymers, and copolymers and blends of these polymers with polymers such as poly(alpha-hydroxy acids) such as lactic, glycolic and hydroxybutyric acids, polycaprolactones, and polyvalerolactones. Polyoxyalkylene copolymers are sold by BASF and others under the tradename Pluronic™. Two acceptable compounds are Pluronic acid F127 and F108, which are PEO-PPO block copolymers with molecular weights of 12,600 and 14,600, respectively. Each of these compounds is available from BASF of Mount Olive, N.J. Pluronic acid F108 at 20-28% concentration, in phosphate buffered saline (PBS) is an example of a suitable LCST material. One beneficial preparation is 22.5% Pluronic acid F108 in PBS. A preparation of 22% Pluronic acid F108 in PBS has an LCST of 37° C. Pluronic acid F127 at 20-35% concentration in PBS is another example of a suitable LCST material. A preparation of 20% Pluronic acid F127 in PBS has an LCST of 37° C. Typical molecular weights are between 5,000 and 25,000, and, for the two specific compounds identified above are 12,600 and 14,600. Pluronic acid F67 is also available for mixtures with other gel materials. Another example is a styrene-butadiene-styrene block copolymer from Polymer Concept Technologies, C-flex™. Further information regarding LCST materials can be found in U.S. Pat. Nos. 6,565,530 B2 and 6,544,227 B2, each to Sahatjian et al., and U.S. Patent Application Pub. No. 2001/0047147 to Slepian et al., each of which is hereby incorporated by reference. Again, once a bead is formed, one or more encapsulation layers can be provided, as desired.

Particularly beneficial core materials (other than cells) include extracellular materials such as submucosa, bone marrow ECM, and basement membrane; various components of extracellular materials, including fibrous materials and ground substance (e.g., glycosaminoglycans, proteoglycans, and glycoproteins), for instance, collagen, laminin, elastin, fibronectin, heparin sulfate, hyaluron dermatan sulfate, keratin sulfate, and chrondroitin sulfate; and various biodegradable polymers, including polyglycolic acid, polylactic acid, poly-2-hydroxy-butyrate, polycaprolactone and copolymers containing the same, such as poly(lactic-co-glycolic) acid, among other materials. These materials can correspond to materials that are used for core formation (e.g., polyelectrolytes, etc.), or they can supplement such materials.

Particularly beneficial shell materials, several of which are also listed above, include submucosa (perforated), and various biodegradable polymers, including those listed in the prior paragraph.

In accordance with certain embodiments of the invention, the outer surfaces of the microcapsules are provided with adhesive species that enhance adhesion to entities that are present in the carrier medium, that are present in adjacent luminal tissue, or both. For example, the encapsulation structure (i.e., shell) can consist of or comprise one or more adhesive species that promote attachment to cells and other components found in lumen walls (e.g., by providing them separately within the encapsulation structure or by linking them to other materials in the encapsulation structure).

Examples of adhesive species include ankyrins, cadherins (calcium dependent adhesion molecules), N-CAMs (calcium independent adhesive molecules), connexins, immunoglobulins, mucoadhesives, sialyl Lex, plant or bacterial lectins (adhesion molecules which specifically bind to sugar moieties of the epithelial cell membrane), integrins, laminins, dermatan sulphate, entactin, fibrin, fibronectin, vimentin, collagen, glycolipids, glycophorin, glycoproteins, heparan sulphate, heparin sulphate, hyaluronic acid, keratan sulphate, proteoglycans, spektrin, von Willebrand factor, vinculin, vitronectin, and polypeptides and proteins containing RGD tripeptide (i.e., ArgGlyAsp, which has been identified to be responsible for some of the cell adhesion properties of fibronectin, laminin, collagen I, collagen IV, thrombospondin, and tenascin), REDV tetrapeptide (i.e., Arg-Glu-Asp-Val), which has been shown to support endothelial cell adhesion but not that of smooth muscle cells, fibroblasts, or platelets), and YIGSR pentapeptide (i.e., TyrIleGlySerArg, which promotes epithelial cell attachment, but not platelet adhesion). More information on RGD, REDV, and YIGSR peptides can be found in U.S. Pat. No. 6,156,572 and U.S. Patent Application No. 2003/0087111.

Many of these species exhibit highly selective interactions such as ligand-receptor or antibody-antigen type interactions. Others, including various mucoadhesives, exhibit more broad-based adhesion. Mucoadhesives commonly have free carboxylic acid or other anionic groups (e.g., sulfonic acid groups). Specific examples of mucoadhesives, non-exclusive of the mucoadhesives listed in the prior paragraph, include the following: acrylic acid polymers and copolymers (e.g., carbomer and derivatives such as carbopol and polycarbophil), poloxamers, celluloses such as methyl cellulose, polyvinyl alcohol, carboxymethyl cellulose and salts thereof, carboxyethyl cellulose and salts thereof, hydroxypropylmethyl cellulose, chitin, chitosan, chondroitin, hyaluronic acid and other glycosaminoglycans, pectin, gelatin, gums such as guar gum, xanthan gum, arabic gum, and tracanth, agarose, alginates.

Because many of these species are polyanions, they can be used in many of the above-described encapsulation/core forming techniques. Moreover, other species (e.g., poloxamer, agarose, etc.) can be solidified into beads via thermal transitions, as also described above.

As noted above, in the compositions of the invention, encapsulated mammalian cells are administered to the body lumen in association with a carrier medium, which inter alia, promotes endoluminal attachment of the composition. The carrier medium is also selected to be physiologically compatible with the cells contained within the microcapsules and with the luminal tissue to which it is applied.

Particularly beneficial carrier media for use in conjunction with the present invention are those which can be administered to the lumen interior in a form that allows the composition to flow and conform itself to the lumen wall, and which are retained in substantial quantities at the site of administration.

In general, the carrier media are polymeric, by which is meant that they comprise one or more polymers, including polymers, macromers, etc. These materials can be soluble or insoluble, natural or synthetic, bioabsorbable or nonbioabsorbable (although bioabsorbable is preferred). The polymers can be homopolymers, copolymers or polymer blends. In various embodiments, the polymers used in the carrier media are hydrogels (this is also true of many of the encapsulation/core forming materials discussed above). As used herein, a hydrogel is defined as a polymeric phase which contains at least 10 wt % water.

Carrier media for use in conjunction with the present invention can be provided in a variety of fluid forms (i.e., forms that are capable of flowing), including solutions, suspensions, dispersions, pastes, gels, and so forth. Polymeric materials within the carrier media can be rendered more solid via a variety of mechanisms. For example, the carrier media can solidify from changes in temperature, they can be polymerizable in response to the formation of ions or free radicals (e.g., via photopolymerization), or they can be covalently or ionically crosslinkable.

Consequently, the polymeric materials in the carrier media can be crosslinked, polymerized or otherwise solidified using a variety of measures, including the following: (a) the application of exogenous measures, for example, the application of heating, cooling, ultrasound, radiation (e.g., infrared, visible, ultraviolet, etc.), the application of a polymerization agent, crosslinking agent, chelating agent, or catalyst, and so forth, and (b) the use of endogenous factors, for example, a change in pH to physiological pH, diffusion of endogenous chemical species into the polymeric material such as calcium ions (e.g., with respect to alginate) or borate ions (e.g., with respect to polyvinyl alcohol), a change in temperature to body temperature, and so forth. Further information can be found, for example, in U.S. Patent Application Pub. No. 2001/0047147 to Slepian et al.

For example, carrier media in accordance with the present invention can be formed using materials, typically polymers, that exist as a liquid at a first temperature, but which solidify when heated. Several LCST materials suitable for this purpose are discussed above. When used as a carrier medium, these materials are applied as viscous fluid at room temperature or lower, and they solidify at the higher temperature of the body after application to the lumen surface.

Other carrier media contain materials, typically polymers, which are in liquid form at an elevated temperature but which become solids at body temperature. For example, thermosetting biodegradable polymers for in vivo use are described in U.S. Pat. No. 4,938,763 to Dunn, et al.

In other embodiments, the carrier media comprise materials that undergo crosslinking in the presence of multivalent ions. Various ionically crosslinkable polymers and multivalent ions suitable for this purpose are set forth above. A particularly beneficial polymer for this purpose is alginate, which undergoes crosslinking, in the presence of endogenous ions such as calcium, barium, magnesium, copper, and iron. Alternatively, these ions can be administered prior to, or following, the application of the composition to the lumen.

With respect to covalent crosslinking, any amino containing polymer can be covalently crosslinked using difunctional reagents, for instance, a dialdehyde such as glutaraldehyde or succindialdehyde. Examples of useful amino containing polymers include polypeptides and proteins.

Materials that can be polymerized, grafted and/or crosslinked using photopolymerization are commonly unsaturated materials which contain a double bond or triple bond. Examples of suitable materials include monomers and macromers that can be polymerized into poly(acrylic acids) (i.e., various Carbopol™ products), poly(acrylates), polyacrylamides, polyvinyl alcohols, acrylated polyethylene glycols, ethylene vinyl acetates, and so forth. Photopolymerization commonly requires the presence of a photosensitizer, photoinitiator, and/or other substance that promotes polymerization. Photopolymerization can be triggered by applying radiation of appropriate wavelength to a cyclo-dimerizable systems such as coumarin and cinnamic acid derivatives. The radiolysis of olefinic monomers results in the formation of cations, anions, and free radicals, all of which initiate chain polymerization, grafting and crosslinking and can be used to polymerize the same monomers and macromers as with photopolymerization. The backbone of alpha-hydroxy acids can be activated to carbonium ions for polymerization. —COOH or —SO$_3$H functionalities can be inserted or provided, which can be subsequently reacted to amine containing ligands.

Adhesion of the carrier media with cells or other components found at the lumen wall can be enhanced by the inclusion of one or more adhesive species. Suitable adhesive species can be selected, for example, from those listed above. Such species can be included, for example, by providing them separately or by linking them to other materials in the carrier medium.

Other adhesive species for use in the carrier media of the present invention include various glues to promote both internal cohesion and lumen adhesion. For example, fibrin glues are advantageous in that they can be easily formed, for example, using the patient's own bodily fluids, or by addition of thrombin and calcium chloride.

Mucous (e.g., a solution of mucin and saline) can also be used in the carrier media.

In some embodiments, the compositions of the present invention are provided with a desiccant after delivery to thicken the carrier media and help hold the compositions in place.

The carrier media for use in the present invention can also optionally comprise various additional agents, examples of which include thickeners or viscosity modifying agents, agents to create a suitable pH and osmotic environment (e.g., buffers, physiological salts, etc.), agents providing cell nutrition, contrast agents to increase visibility (e.g., color indicators, ultrasonic contrast agents, NMR contrast agents, radiological contrast agents), and/or one or more bioactive agents.

"Bioactive agents", "therapeutic agents", "pharmaceutically active agents", "drugs" and other related terms may be used interchangeably herein and include genetic bioactive agents and non-genetic bioactive agents. Bioactive agents may be used singly or in combination.

Exemplary non-genetic bioactive agents for use in connection with the present invention include: (a) anti-thrombotic agents such as heparin, heparin derivatives, urokinase, and PPack (dextrophenylalanine proline arginine chloromethylketone); (b) steroidal and non-steroidal anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, antithrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin and prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin; (t) beta-blockers, (u) bARKct inhibitors, (v) phospholamban inhibitors, (w) Serca 2 gene/protein; (x) antibiotics; (y) antivirals; (z) anti-spasmodics including channel blockers; (aa) tissue plasminogen activator (TPA), anisoylated plasminogen activator (TPA) and anisoylated plasminogen-streptokinase activator complex (APSAC); (bb) extracellular matrix components, their derivatives, and their receptors, and (cc) other agents which may modulate tissue tone, function, and the healing response to organ injury post intervention.

Exemplary genetic bioactive agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation.

Vectors for delivery of genetic bioactive agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP), SP1017 (SUPRATEK), lipids such as cationic lipids, liposomes, lipoplexes, nanoparticles, or microparticles, with and without targeting sequences such as the protein transduction domain (PTD).

Numerous bioactive agents, not necessarily exclusive of those listed above, have been identified as candidates for vascular treatment regimens. Such agents are useful for the practice of the present invention and include one or more of the following: (a) Ca-channel blockers including benzothiazepines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK (D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguaiaretic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional bioactive agents useful for the practice of the present invention are also disclosed in U.S. Pat. No. 5,733,925 assigned to NeoRx Corporation, the entire disclosure of which is incorporated by reference.

A wide range of bioactive agent loadings can be used in connection with the dosage forms of the present invention, with the pharmaceutically effective amount being readily determined by those of ordinary skill in the art and ultimately depending, for example, the nature of the bioactive agent itself, the tissue to which the dosage form is introduced, and so forth.

The compositions of the present invention can be applied using a variety of medical devices and techniques, depending, for example, on the particular lumen being treated, the nature of the composition being applied to the lumen, and so forth.

Suitable medical devices include those that are adapted for endoluminal delivery of therapeutic compositions, and include catheters and other devices capable of applying therapeutic compositions in accordance with the present invention to lumen walls, for example, by spraying, extrusion, physical transfer (e.g., brushing, rolling, etc.). In some instances, the medical device is equipped to introduce two or more compositions (e.g., a composition containing a carrier medium with dispersed microcapsules and a solidifying composition, e.g., a crosslinking/polymerizing composition, desiccant composition, etc.).

In some embodiments, the medical devices are equipped to introduce or remove energy to promote solidification of the applied compositions. For example, heat can be removed by spraying with a chilled fluid or introducing a chilled fluid into a catheter balloon, and heat can be added by spraying with a heated fluid, by introducing a heated fluid into a catheter balloon, by electrical heating, by inductive heating, and so forth. Energy can also be introduced, for example, by incorporating a radiation-emitting component into the device, which is suitable for delivery of infrared, visible, ultraviolet, radiofrequency (e.g., microwave), or other type of radiation to the composition.

In certain embodiments, multiple layers of the compositions of the present invention are applied to a body lumen, each with differing types of microencapsulated cells, differing microcapsule core materials, and/or differing carrier media materials, which will allow the as-applied compositions to mimic the physiology of the cells being replaced better. For example, in treating a vascular site, a first layer can be applied, which contains ECM components, encapsulated fibroblasts and/or smooth muscle cells, and a second layer can be applied, which contains encapsulated squamous epithelial cells, vascular cells or endothelial cells, or parent cells of the same, such as stem cells.

Figure 3A:
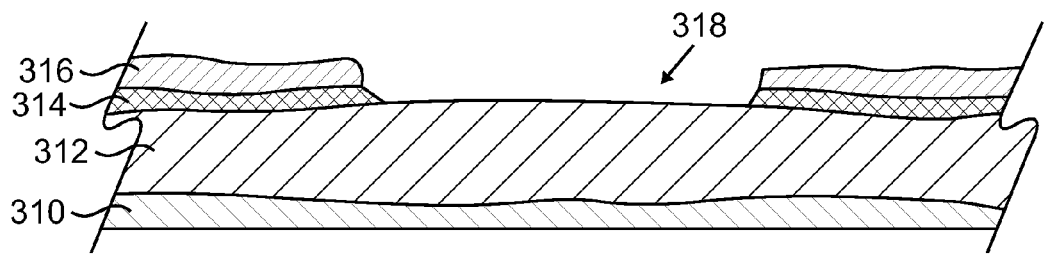
FIGS. 3A to 3D are schematic illustrations depicting the use of a tissue engineering composition of the present invention for the treatment of a site produced by the surgical removal of abnormal columnar cells (i.e., Barrett's epithelium) from the region of the lower esophageal sphincter of a patient suffering from gastroesophageal reflux disease.

A specific example will now be described with respect to FIGS. 3A-3D. Referring to FIG. 3A, an opening 318 in the mucosal 316 and submucosal 314 tissue layers on the esophageal surface is shown, which is due to the surgical removal of abnormal columnar cells (i.e., Barrett's epithelium) from the region of the lower esophageal sphincter of a patient suffering from gastroesophageal reflux disease. Also illustrated are the muscularis 312 and serosa 310.

Figure 3B:
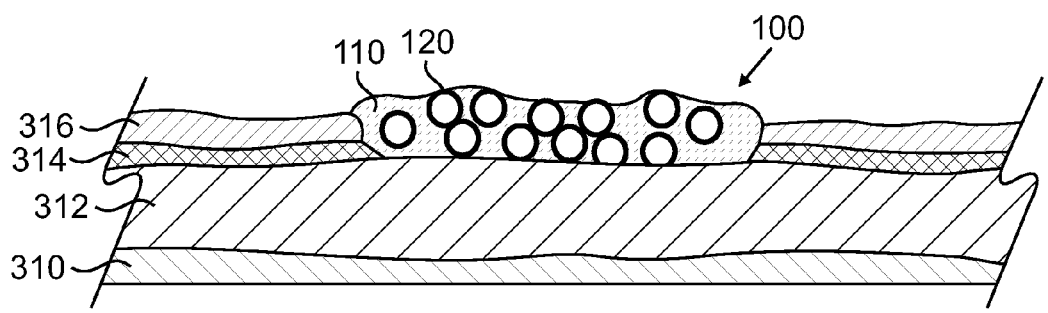

Referring now to FIG. 3B, a tissue engineering composition 100 in accordance with the present invention, which contains encapsulated squamous epithelial cells 120 dispersed in an appropriate carrier medium 110, is applied to the fill the opening 318 shown in FIG. 3A. The tissue engineering composition 100 may be applied, for example, using a catheter that has been guided to the lesion through the working channel of an endoscope (not illustrated). For instance, the proximal end of the catheter may be fitted with a syringe filled with the tissue engineering composition, and used to force the composition out of the distal end of the catheter and onto the lesion. An advantage of such a procedure is that, with selection of a sufficiently flexible carrier medium (e.g., a hydrogel), peristalsis will not be inhibited, the composition will move with (and thus not tear away from) the esophageal wall during peristalsis. The composition also conforms to irregularities on the surface of the esophageal wall.

Figure 3C:
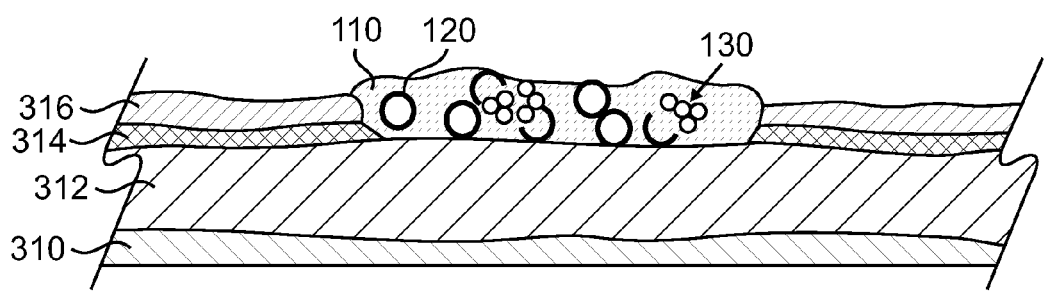
Figure 3D:
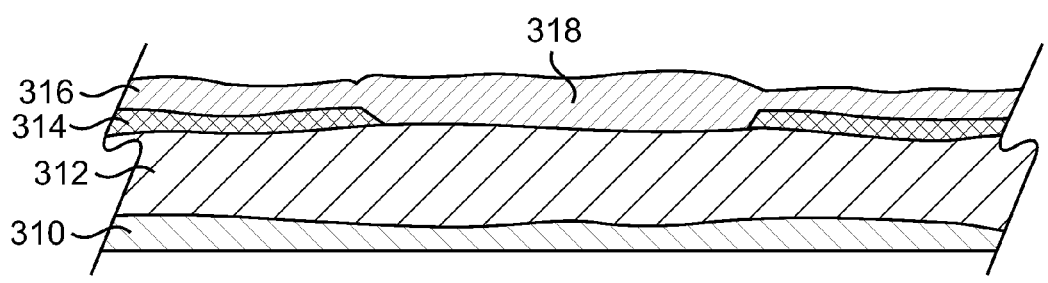

Over time, the cells within the microcapsules 120 begin to divide and the outer shell degrades, releasing squamous epithelial cells 130 as illustrated in FIG. 3C. The cultured cells continue to proliferate under the influence of the nutrients and growth hormones provided by the composition and/or the host and insinuate themselves into the treatment site. At the same time healthy tissue surrounding the lesion is also stimulated to proliferate, and a layer of healthy endothelial tissue 318 is eventually created, as shown in FIG. 3D.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A tissue engineering composition for application to an interior surface of a body lumen of a patient, said composition comprising (a) a carrier medium that is adapted to flow and stably adhere said composition to said body lumen, said carrier medium comprising collagen as an adhesion agent and (b) microcapsules dispersed within the carrier medium, which comprise one or more living cells encapsulated within a coating that comprises a biodegradable polymer, wherein said composition promotes growth of said cells on said lumen surface subsequent to application of said composition to said lumen.

2. The tissue engineering composition of claim 1, wherein said carrier medium is an ionically crosslinkable composition.

3. The tissue engineering composition of claim 1, wherein said carrier medium is a thermosensitive composition that solidifies upon a change in temperature.

4. The tissue engineering composition of claim 1, wherein said carrier medium further comprises an adhesion promoting component selected from fibrinogen, mucin, alginate, fibronectin, and combinations thereof.

5. The tissue engineering composition of claim 1, wherein said carrier medium further comprises a bioactive agent selected from antibiotics, antivirals, anesthetics, growth factors, extracellular matrix components, and combinations thereof.

6. The tissue engineering composition of claim 1, wherein said carrier medium further comprises an agent selected from viscosity modifying agents, buffers, osmotic agents, nutritional agents, contrast agents and combinations thereof.

7. The tissue engineering composition of claim 1, wherein a majority of said microcapsules range from 10 to 1000 microns in diameter.

8. The tissue engineering composition of claim 1, wherein at least a portion of said microcapsules comprise a conformal polyelectrolyte coating surrounding single living cells or aggregates of living cells.

9. The tissue engineering composition of claim 8, wherein said polyelectrolyte coating comprises a polyanion layer and a polycation layer.

10. The tissue engineering composition of claim 1, wherein at least a portion of said microcapsules comprise (a) a core comprising a plurality of living cells or living cell aggregates and (b) a permeable shell surrounding said core.

11. The tissue engineering composition of claim 10, wherein said core further comprises a material selected from extracellular matrix, isolated extracellular matrix components, and combinations thereof.

12. The tissue engineering composition of claim 10, wherein said core further comprises a material selected from submucosa, bone marrow, extracellular matrix, isolated extracellular matrix components, basement membrane, collagen, glycosaminoglycans, proteoglycans, glycoproteins, polyglycolic acid, polylactic acid, poly(lactic-co-glycolic) acid, and combinations thereof.

13. The tissue engineering composition of claim 10, wherein said shell comprises a material selected from extracellular matrix, isolated extracellular matrix components, biodegradable polymers, self-assembling polymers, and combinations thereof.

14. The tissue engineering composition of claim 10, wherein said shell comprises a material selected from perforated submucosa, polyglycolic acid, polylactic acid, poly(lactic-co-glycolic)acid, and combinations thereof.

15. The tissue engineering composition of claim 10, wherein the shell comprises a polyanion layer and a polycation layer.

16. The tissue engineering composition of claim 1, wherein outer surfaces of said microcapsules comprise an adhesive species.

17. The tissue engineering composition of claim 16, wherein said adhesive species are selected from mucoadhesives, antibodies, attachment ligands, adhesion proteins, cell surface molecules, and combinations thereof.

18. The tissue engineering composition of claim 1, wherein said cells are selected from epithelial cells, cardiomyocytes, smooth muscle cells, fibroblasts, stem cells, mesenchymal stem cells, and combinations thereof.

19. The tissue engineering composition of claim 1, wherein said cells are selected from squamous epithelial cells, vascular endothelial cells and a combination thereof.

20. The tissue engineering composition of claim 1, wherein said cells comprise stem cells.

21. A tissue engineering composition for application to an interior surface of a body lumen of a patient, said composition comprising (a) a carrier medium that is adapted to flow and stably adhere said composition to said body lumen, said carrier medium comprising collagen and (b) microcapsules dispersed within the carrier medium which comprise a core that comprises extracellular matrix or isolated extracellular matrix components and one or more living stem cells encapsulated within a coating that comprises a biodegradable polymer, wherein said composition promotes growth of said cells on said lumen surface subsequent to application of said composition to said lumen.

22. A tissue engineering composition for application to an interior surface of a body lumen of a patient, said composition comprising (a) a carrier medium that is adapted to flow and stably adhere said composition to said body lumen and (b) microcapsules dispersed within the carrier medium, which comprise one or more living cells and a material selected from extracellular matrix and isolated extracellular matrix components encapsulated within a coating that comprises a biodegradable polymer, wherein said composition promotes growth of said cells on said lumen surface subsequent to application of said composition to said lumen.

23. The tissue engineering composition of claim 22, wherein said cells are living stem cells.

* * * * *